United States Patent
Burckhardt et al.

(10) Patent No.: US 7,030,384 B2
(45) Date of Patent: Apr. 18, 2006

(54) ADAPTIVE OPTO-EMISSION IMAGING DEVICE AND METHOD THEREOF

(75) Inventors: Darrell D. Burckhardt, Hoffman Estates, IL (US); Douglas J. Wagenaar, South Barrington, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 192 days.

(21) Appl. No.: 10/187,997

(22) Filed: Jul. 3, 2002

(65) Prior Publication Data

US 2004/0005028 A1    Jan. 8, 2004

(51) Int. Cl.
*G01T 1/161* (2006.01)

(52) U.S. Cl. .............................. 250/370.09; 378/98.5; 378/98.8

(58) Field of Classification Search .................. 378/98, 378/98.2, 98.5, 98.8, 189; 250/370.09, 370.08, 250/370.07; 600/407, 436
See application file for complete search history.

(56) References Cited

U.S. PATENT DOCUMENTS

| | | | | |
|---|---|---|---|---|
| 3,011,057 | A * | 11/1961 | Anger | 250/366 |
| 3,860,821 | A * | 1/1975 | Barrett | 250/363.01 |
| 3,936,646 | A * | 2/1976 | Jonker | 378/148 |
| 4,497,769 | A * | 2/1985 | Nicholson et al. | 250/362 |
| 5,208,675 | A * | 5/1993 | Wilson et al. | 348/370 |
| 5,732,704 | A | 3/1998 | Thurston et al. | |
| 5,840,012 | A * | 11/1998 | Krauter et al. | 600/102 |
| 5,851,183 | A | 12/1998 | Bucholz | |
| 5,916,167 | A | 6/1999 | Kramer et al. | |
| 5,932,879 | A | 8/1999 | Raylman et al. | |
| 5,961,458 | A | 10/1999 | Carroll | |
| 6,021,341 | A | 2/2000 | Scibilia et al. | |
| 6,088,424 | A * | 7/2000 | Postlethwaite et al. | 378/63 |
| 6,204,505 | B1 | 3/2001 | Call | |
| 6,392,235 | B1 * | 5/2002 | Barrett et al. | 250/363.06 |
| 6,495,834 | B1 * | 12/2002 | Corvo et al. | 250/363.1 |
| 6,590,958 | B1 * | 7/2003 | Barber et al. | 378/98.8 |
| 2003/0081716 | A1 * | 5/2003 | Tumer | 378/19 |
| 2003/0179308 | A1 * | 9/2003 | Zamorano et al. | 348/333.12 |

FOREIGN PATENT DOCUMENTS

WO    WO 9852071 A1 * 11/1998
WO    WO 200277668 A1 * 10/2002

OTHER PUBLICATIONS

Redus et al., "An Imaging Nuclear Survey System", IEEE Transactions on Nuclear Science, vol. 43, No. 3, Jun. 1996, pps. 1827-1831.*

* cited by examiner

*Primary Examiner*—Edward J. Glick
*Assistant Examiner*—Chih-Cheng Glen Kao

(57) ABSTRACT

An adaptive opto-emission imaging device includes a detector having a detector face and a back surface. The detector detects radiation emanating from an object positioned in the direction of the detector face, and produces a radiopharmaceutical distribution profile of the detected radiation. An image capturing device such as a video camera provided at the detector face of the detector produces a live visual image of the object. A display device provided at the back surface of the detector displays the radiopharmaceutical distribution profile and/or the live visual image of the object. The adaptive opto-emission imaging device greatly reduces the amount of computation and time to provide real time image guidance, for example to physicians using the device to perform an image-guided surgical procedure.

15 Claims, 2 Drawing Sheets

ADAPTIVE OPTO-EMISSION IMAGING DEVICE AND METHOD THEREOF

BACKGROUND OF THE INVENTION

1. Field of the Invention

The present invention relates generally to an adaptive opto-emission imaging device and method thereof. Specifically, the invention relates to a method and an apparatus for reducing the amount of computation and time to provide real time image guidance during surgery.

2. Description of the Background Art

Nuclear medicine (NM) has provided physicians with important diagnostic and functional information on specific organs, tissues and disease states. NM is employed primarily for the detection of disease in cardiology, oncology and neurology. It provides functional information e.g., metabolism, perfusion and tissue typing and differentiation, that other methods cannot.

Radiographic imaging is the detection of radiation in order to form an image. By detecting the amount of radiation emanating from a test subject, the resultant image may give a representative view of the structure of the test subject.

Radiographic imaging typically employs gamma rays. Gamma rays are a form of radiation that is emitted by excited atomic nuclei during the process of passing to a lower excitation state. Gamma radiation is capable of passing through soft tissue and bone. Gamma radiation may be provided by a radiopharmaceutical, such as thallium or technetium, for example, that is administered to the patient. The radiopharmaceutical travels through the patient's body, and may be chosen to be absorbed or retained by an object (i.e., an organ of interest). The radiopharmaceutical generates a predictable emission of gamma rays through the patient's body that can be detected and used to create an image.

A radiographic imaging device may be used to detect radiation emanating from the patient and may be used to form an image or images for viewing and diagnosis. The radiographic imaging device may be a device such as a gamma or gamma ray camera, also referred to as a scintillation camera or an Anger camera. The radiographic imaging device allows a doctor to perform a diagnosis on a patient in a non-invasive manner and additionally may allow the doctor to observe organ function. In addition, the radiographic imaging device may be used for other imaging functions.

A radiographic imaging device typically contains one or more radiographic sensor modules, such as a solid state detector module. The detector may be a module made of cadmium zinc telluride (CZT) that generates an electrical signal representative of the location of gamma ray interaction and the energy of the gamma ray in the detector material. The accumulated counts at each stored location (as stored in a memory device) may be used to create an image of the distributed radiation field of interest.

Surgical probes may also be used to detect tissues emitting gamma radiation as a guide to a surgeon. The probes' sensitivity to gamma radiations may give analogic signals whose numbers are proportional to the detected radiopharmaceutical concentration. As details of conventional surgical probes are available in numerous publications and patents including, by way of example, U.S. Pat. No. 6,204,505 (Call), U.S. Pat. No. 6,021,341 (Scibilia et al.), U.S. Pat. No. 5,961,458 (Carroll), U.S. Pat. No. 5,932,879 (Raylman), U.S. Pat. No. 5,916,167 (Kramer et al.), U.S. Pat. No. 5,851,183 (Bucholz) and U.S. Pat. No. 5,732,704 (Thurston et al.), no attempt is made herein to provide a detailed description of such devices.

Anatomical imaging modalities are currently used for image guidance. These include digital subtraction angiography (DSA), computed tomography (CT), ultrasound (US), and magnetic resonance imaging (MRI). During anatomical image-guided surgery, patient images acquired intra-operatively are aligned with scans acquired pre-operatively from one or more of the imaging modalities listed above. High performance computing is critically important to achieve accurate intra-operative images in a time frame compatible with surgical intervention. As these procedures expand into routine clinical medicine, it is increasingly clear that image fusion and registration technology have their limitations in dealing with tissue deformation occurring during a surgical task. The accuracy of data, memory and computationally intensive segmentation algorithms are significantly important. However, tradeoffs in image quality and accuracy are necessary to provide fast intra-operative images.

There is therefore a need for an imaging device that reduces the amount of computation and time to provide real time image guidance, and high quality, accurate intra-operative images.

There is also a need for an imaging device that is noninvasive and non-restrictive in projecting tumor and areas differentiated by radiation emitting tissues that lie below the visible surface (i.e., organs affected by tumor).

SUMMARY OF THE INVENTION

A first aspect of the invention is generally applicable to an adaptive opto-emission imaging device. The adaptive opto-emission imaging device includes a detector having a detector face and a back surface. The detector detects radiation emanating from an object positioned in the direction of the detector face, and produces a radiopharmaceutical distribution profile of the detected radiation. An image capturing device provided at the detector face of the detector produces a live visual image of the object. A display device provided at the back surface of the detector displays the radiopharmaceutical distribution profile and/or the visual image of the object.

A second aspect of the present invention is generally applicable to a method of providing a live visual image of an object obscured by a radiation detector for detecting radiation emanating from within the object. The method comprises the steps of providing a radiation detector for detecting radiation emanating from an object positioned in a direction of a face of the detector, producing a radiopharmaceutical distribution profile of the detected radiation, and providing an image capturing device on the detector face for producing a live visual image of the object positioned in the direction of the detector face. Also included is the step of displaying the radiopharmaceutical distribution profile and/or the anatomical structure of the object on a display mounted to a back surface of the detector opposite the detector face.

The above and other features and advantages of the present invention will be further understood from the following description of the preferred embodiment thereof, taken in conjunction with the accompanying drawings wherein like reference numerals are used throughout the various views to designate like parts.

BRIEF DESCRIPTION OF THE DRAWINGS

FIG. 1a is a schematic view illustrating the side of the imaging device, FIG. 1b is a schematic view illustrating the front (far side) of the imaging device, and FIG. 1c is a schematic view illustrating the back (near side) of the imaging device.

DETAILED DESCRIPTION OF THE PREFERRED EMBODIMENTS

Figure 1C:
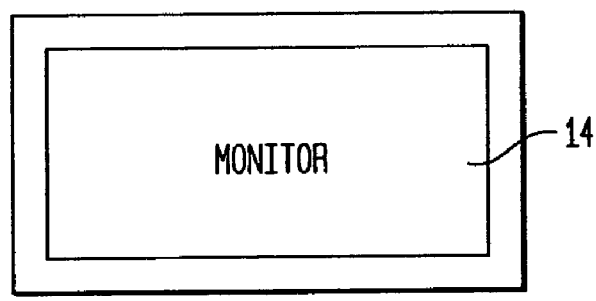
FIGS. 1a through 1c are schematic views illustrating an embodiment of an adaptive opto-emission imaging device according to the present invention.
Figure 1A:
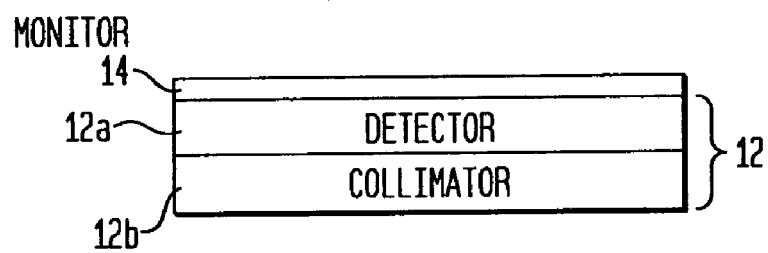
Figure 1B:
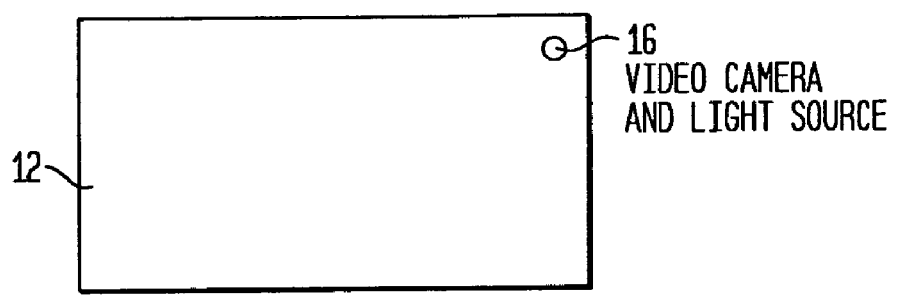

An embodiment of an adaptive opto-emission imaging device 10 according to the present invention is shown in FIGS. 1a through 1c. FIG. 1a is a schematic view illustrating the side of the imaging device 10, FIG. 1b is a schematic view illustrating the front (far side) of the imaging device 10, and FIG. 1c is a schematic view illustrating the back (near side) of the imaging device 10.

The imaging device 10 can be portable and used for diagnosis, risk assessment, monitoring, intervention, or the like. Further, the imaging device 10 can be suitable for use in an emergency room, hybrid surgical suit, cardiovascular lab, general practitioner's office, radiology or nuclear medicine department, radiopharmacy or hot lab, small animal imaging laboratory, or the like. Referring to FIGS. 1a through 1c, the imaging device 10 generally includes a collimated CZT detector 12, a display panel or monitor 14, and a solid state video camera and light source 16. The detector 12 is configured to detect the shape and location of gamma radiation. The video camera 16 located at the face of the detector 12 is configured to provide a video image. The display panel 14 attached to the back (near side) of the detector 12 is configured to display live video images (e.g., an anatomical structure of an object) produced by the video camera 16 along with the shape and location information of the gamma radiation (e.g., a radiopharmaceutical distribution profile) detected by the detector 12. The detector 12, the display panel 14, and the video camera and light source 16 may be contained in a housing.

The collimated CZT detector 12 may include a thin gamma radiation detector 12a and a short bore collimator 12b. It will be appreciated that any means for detecting radiation emanating from an object may be implemented as the detector 12. The detector 12 has a detector face (far side), as shown in FIG. 1b, and a back panel or surface (near side), as shown in FIG. 1c. The video camera and light source 16 can be mounted on the far side or detector face of the detector 12. The video camera 16 can be a live video camera. The display panel 14 can be attached to the near side or back surface of the detector 12. The display panel 14 can be a flat, liquid crystal, color display panel. The display panel 14 may also be a monochrome display panel.

The imaging device 10 can be hand held or supported by a "hands free" articulating arm (not shown) that can be passively controlled by the hand, or actively controlled through the use of switches on a foot console. The imaging device 10 can be easily and expeditiously adjusted in proximity to an object or an area of interest. Information and data may be recorded and operative procedures may be observed without disrupting the movements of the physicians. Visual images displayed on the display panel 14 may be viewed or adjusted using features such as focus, pan, zoom and scroll.

Figure 2:
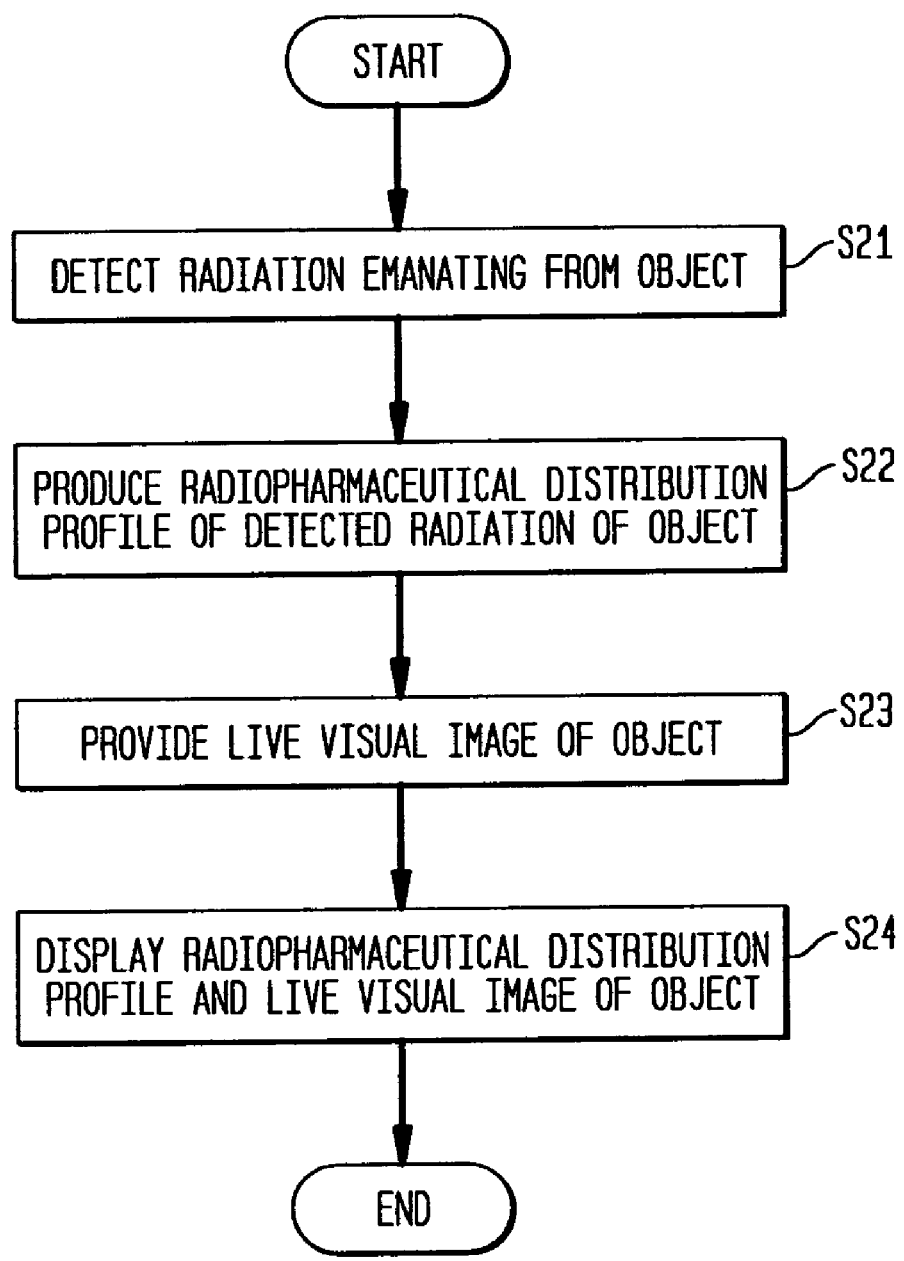
FIG. 2 is a flowchart illustrating details of a method of providing a live image of an object obscured by a radiation detector of the imaging device of FIG. 1.

Next, the operation of the adaptive opto-emission imaging device 10 according to the present invention will now be described with reference to FIG. 2.

An object (not shown) is positioned in the direction of the detector face of the detector 12 of the imaging device 10. The imaging device 10 provides a smaller field-of-view focusing on a region of interest. Radiation emanating from the object is detected by the detector 12 in step S21. Any form of emission imaging (e.g., any wavelength of light including visible to the human eye) emitted from the object can be detected by the detector 12 and associated video camera 16. Also, the emission of fluorescent light from obscured objects where the fluorescence is stimulated by a bath of laser or other source of light within a given range of wavelengths will be detected. The shape and location information of the gamma radiation detected by the detector 12 are stored for processing in step S22.

In step S23, the video camera 16 provides live visual images of the object and the data are stored for processing. Signals of the processed data are transmitted to the display panel 14. The display panel 14 displays the radiation distribution information detected by the detector 12, along with live visual images provided by the video camera 16 for viewing by an operator in step S24. The image displayed on the display panel 14 depicts the anatomical structure and the radiopharmaceutical distribution profile of the object, thereby providing immediate identification, and if necessary, surgical intervention of the diseased structure. Accordingly, the imaging device 10 enables the live visual mix of human anatomy and its associated radioactivity distribution profile of the object or area of interest. Alternatively, the anatomical structure or the radiopharmaceutical distribution profile of the object may be displayed separately on the display panel 14, rather than the combined image.

Further, the storage of views from previous vantage points may allow the computation of an enhanced 3-dimensional, solid-modeled, virtual-reality rendered, stereo, or holographic image to the displayed image, rather than a simple fused planar image. Additionally, magnification of blended or mixed displays improves localization and visualization of affected tissues by using adjustable features, i.e., focus, color scales, pan, zoom and scroll of the blended scintographic and visual images.

The imaging device 10 provides functional image guidance that can give physicians increased confidence in identifying the properties of tissues and structures that are visible but not necessarily known during surgery. In nonmalignant disease cases, the imaging device 10 may assist in preventing inappropriately aggressive surgery that may harm a patient, and in other cases, it assures the successful eradication of the diseased tissue.

The present invention provides advantages which are not found in the known surgical probe radiation detection systems. For instance, the adaptive opto-emission imaging device 10 is compact and lightweight, and can be used with other imaging modalities (i.e., can be placed in a MR or CT imaging suite). The imaging device 10 is easy to install, adjust and greatly reduces the amount of computation and time to provide real time image guidance. Further, the imaging device 10 utilizes previously acquired information to improve the appearance of the previously acquired information to improve the appearance of the object or structure displayed. Accordingly, areas of interest (i.e., the area to be cut and removed) are better defined without the need of probing through and around the tissue.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed:

1. An adaptive opto-emission imaging device comprising:
   a detector having a detector face and a back surface opposite said detector face, said detector being operable to detect radiopharmaceutical radiation emanating from an object positioned in a direction of said detector face and to produce a radiopharmaceutical distribution profile of the detected radiation;
   an image capturing device provided on said detector face of said detector operable to produce a live visual image of said object; and
   a display device provided on said back surface of said detector that is capable of displaying said radiopharmaceutical distribution profile in alignment with said live visual image of said object as a combined image.

2. The imaging device of claim 1, wherein said radiopharmaceutical distribution profile includes the shape and location of said detected radiation.

3. The imaging device of claim 1, wherein said detector includes a gamma radiation detector and a short bore collimator.

4. The imaging device of claim 1, wherein said image capturing device includes a video camera.

5. The imaging device of claim 1, wherein said display device includes a video monitor.

6. The imaging device of claim 5, wherein said video monitor is a color monitor.

7. The imaging device of claim 1, wherein said detector, said image capturing device, and said display device are contained in a housing.

8. The imaging device of claim 1, wherein said image capturing device includes a light source.

9. A method of providing a live image of an object obscured by a radiation detector for detecting radiopharmaceutical radiation emanating from within said object, comprising the steps of:
   providing a radiation detector for detecting radiation emanating from within an object positioned in a direction of a face of said detector;
   producing a radiopharmaceutical distribution profile of the detected radiation;
   providing an image capturing device on said detector face for producing a live visual image of said object positioned in said direction of said detector face; and
   displaying said radiopharmaceutical distribution profile in alignment with said live visual image of said object as a combined image on a display mounted to a back surface of said detector opposite said detector face.

10. The method of claim 9, wherein said radiopharmaceutical distribution profile includes the shape and location of said detected radiation.

11. The method of claim 9, wherein the step of providing said radiation detector includes the steps of providing a gamma radiation detector and a short bore collimator.

12. The method of claim 9, wherein the step of providing said image capturing device includes the step of providing a video camera.

13. The method of claim 9, wherein said display includes a video monitor.

14. The method of claim 13, wherein said video monitor is a color monitor.

15. The method of claim 9, further comprising the step of providing said detector, said image capturing device, and said display in a single housing.

* * * * *